US012412637B2

(12) United States Patent
Das et al.

(10) Patent No.: US 12,412,637 B2
(45) Date of Patent: Sep. 9, 2025

(54) EMBEDDING-BASED GENERATIVE MODEL FOR PROTEIN DESIGN

(71) Applicant: International Business Machines Corporation, Armonk, NY (US)

(72) Inventors: Payel Das, Yorktown Heights, NY (US); Pin-Yu Chen, White Plains, NY (US); Enara C. Vijil, Westchester, NY (US); Igor Melnyk, White Plains, NY (US); Yue Cao, College Station, TX (US)

(73) Assignee: International Business Machines Corporation, Armonk, NY (US)

( * ) Notice: Subject to any disclaimer, the term of this patent is extended or adjusted under 35 U.S.C. 154(b) by 1157 days.

(21) Appl. No.: 17/317,399

(22) Filed: May 11, 2021

(65) Prior Publication Data

US 2022/0375538 A1 Nov. 24, 2022

(51) Int. Cl.
| | | |
|---|---|---|
| *G16B 15/20* | (2019.01) | |
| *G06F 30/10* | (2020.01) | |
| *G06F 30/27* | (2020.01) | |
| *G06T 19/20* | (2011.01) | |
| *G16B 15/10* | (2019.01) | |
| *G16H 50/50* | (2018.01) | |
| *G16H 50/70* | (2018.01) | |
| *G16H 70/60* | (2018.01) | |

(52) U.S. Cl.
CPC .............. *G16B 15/20* (2019.02); *G06F 30/10* (2020.01); *G06F 30/27* (2020.01); *G06T 19/20* (2013.01); *G16B 15/10* (2019.02); *G06T 2219/2016* (2013.01); *G16H 50/50* (2018.01); *G16H 50/70* (2018.01); *G16H 70/60* (2018.01)

(58) Field of Classification Search
CPC ......... G16B 15/20; G16B 15/10; G06F 30/10; G06F 30/27; G06F 40/126; G06T 19/20; G06T 2219/2016
See application file for complete search history.

(56) References Cited

U.S. PATENT DOCUMENTS

| | | |
|---|---|---|
| 2006/0259247 A1 | 11/2006 | Mayo et al. |
| 2018/0107927 A1 | 4/2018 | Frey |
| 2020/0273541 A1 | 8/2020 | Costello et al. |
| 2022/0270711 A1* | 8/2022 | Feala ..................... G16B 45/00 |

OTHER PUBLICATIONS

Vaswani, A., Shazeer, N., Parmar, N., Uszkoreit, J., Jones, L., Gomez, A.N., Kaiser, Ł. and Polosukhin, I. Attention is all you need. Advances in Neural Information Processing Systems, 30:1-11. (Year: 2017).*
Hernandez, A. and Amigó, J.M. Attention mechanisms and their applications to complex systems. Entropy, 23(3):1-18. (Year: 2021).*
Villegas-Morcillo, A., Makrodimitris, S., van Ham, R.C., Gomez, A.M., Sanchez, V. and Reinders, M.J. Unsupervised protein embeddings outperform hand-crafted sequence and structure features at predicting molecular function. Bioinformatics, 37(2), pp. 162-170. (Year: 2020).*
Amidi, A., Amidi, S., Vlachakis, D., Megalooikonomou, V., Paragios, N. and Zacharaki, E.I.. EnzyNet: enzyme classification using 3D convolutional neural networks on spatial representation. PeerJ, 6:1-18. (Year: 2018).*
Cao et al., "Fold2Seq: A Joint Sequence(1D)-Fold(3D) Embedding-based Generative Model for Protein Design," ICLR 2021 Conference Submission; https://openreview.net/forum?id=1-Mh-cWROZ. Sep. 28, 2020 (modified Mar. 5, 2021). 15 pages.
Ingraham et al., "Generative models for graph-based protein design.".In Advances in Neural Information Processing Systems, 2019. pp. 15820-15831.
Gao et al. "Deep Learning in Protein Structural Modeling and Design," https://arxiv.org/abs/2007.08383. Jul. 16, 2020. 55 pages.
Bepler et al. "Learning Protein Sequence Embeddings Using Information From Structure." ICLR 2019 Conference; https://arxiv.org/abs/1902.08661. Submitted on Feb. 22, 2019 (v1), last revised Oct. 16, 2019 (this version), v2. 17 pages.
Karimi et al. "De Novo Protein Design for Novel Folds Using Guided Conditional Wasserstein Generative Adversarial Networks," Journal of Chemical Information and Modeling; https://pubs.acs.org/doi/abs/10.1021/acs.jcim.0c00593. Sep. 18, 2020. 20 pages.
Grenner et al. "Design of Metalloproteins and Novel Protein folds using Variational Autoencoders." Scientific Reports; DOI: 10.1038/s41598-018-34533-1. Accepted Oct. 19, 2018 and published online Nov. 1, 2018. 12 pages. vol. 8 No. 16189.
Huang et al. "RosettaRemodel: A Generalized Framework for Flexible Backbone Protein Design." PLoS One; https://doi.org/10.1371/journal.pone.0024109. Accepted Jul. 29, 2011 and published Aug. 31, 2011. 10 pages. 6(8): e24109.

(Continued)

*Primary Examiner* — Olivia M. Wise
*Assistant Examiner* — Janna Nicole Schultzhaus
(74) *Attorney, Agent, or Firm* — Scully, Scott, Murphy & Presser, P.C.; Yuanmin Cai

(57) ABSTRACT

A system and method for designing protein sequences conditioned on a specific target fold. The system is a transformer-based generative framework for modeling a complex sequence-structure relationship. To mitigate the heterogeneity between the sequence domain and the fold domain, a Fold-to-Sequence model jointly learns a sequence embedding using a transformer and a fold embedding from the density of secondary structural elements in 3D voxels. The joint sequence-fold representation through novel intra-domain and cross-domain losses with an intra-domain loss forces two semantically similar (where the proteins should have the same fold(s)) samples from the same domain to be close to each other in a latent space, while a cross-domain loss forces two semantically similar samples in different domains to be closer. In an embodiment, the Fold-to-Sequence model performs design tasks that include low resolution structures, structures with a region of missing residues, and NMR structural ensembles.

25 Claims, 7 Drawing Sheets

(56) References Cited

OTHER PUBLICATIONS

Strokach et al. "Fast and flexible design of novel proteins using graph neural networks." bioRxiv; doi: https://doi.org/10.1101/868935. Mar. 14, 2020. 37 Pages.
Wikipedia. "Softmax Function." wikipedia.com; https://en.wikipedia.org/w/index.php?title=Softmax_function&oldid=1007485575. Last edited Feb. 18, 2021. 10 pages.
Alammar, J. "The Illustrated Transformer," https://jalammar.github.io/illustrated-transformer/. Jun. 27, 2018. 22 pages.
Wikipedia. "Multilayer Perceptron," wikipedia.com; https://en.wikipedia.org/w/index.phptitle=Multilayer_perceptron&oldid=1006601092. Last edited on Feb. 13, 2021. 5 pages.
Anonymous. "Average Pooling," Papers With Code; https://paperswithcode.com/method/average-pooling. 3 pages.

* cited by examiner

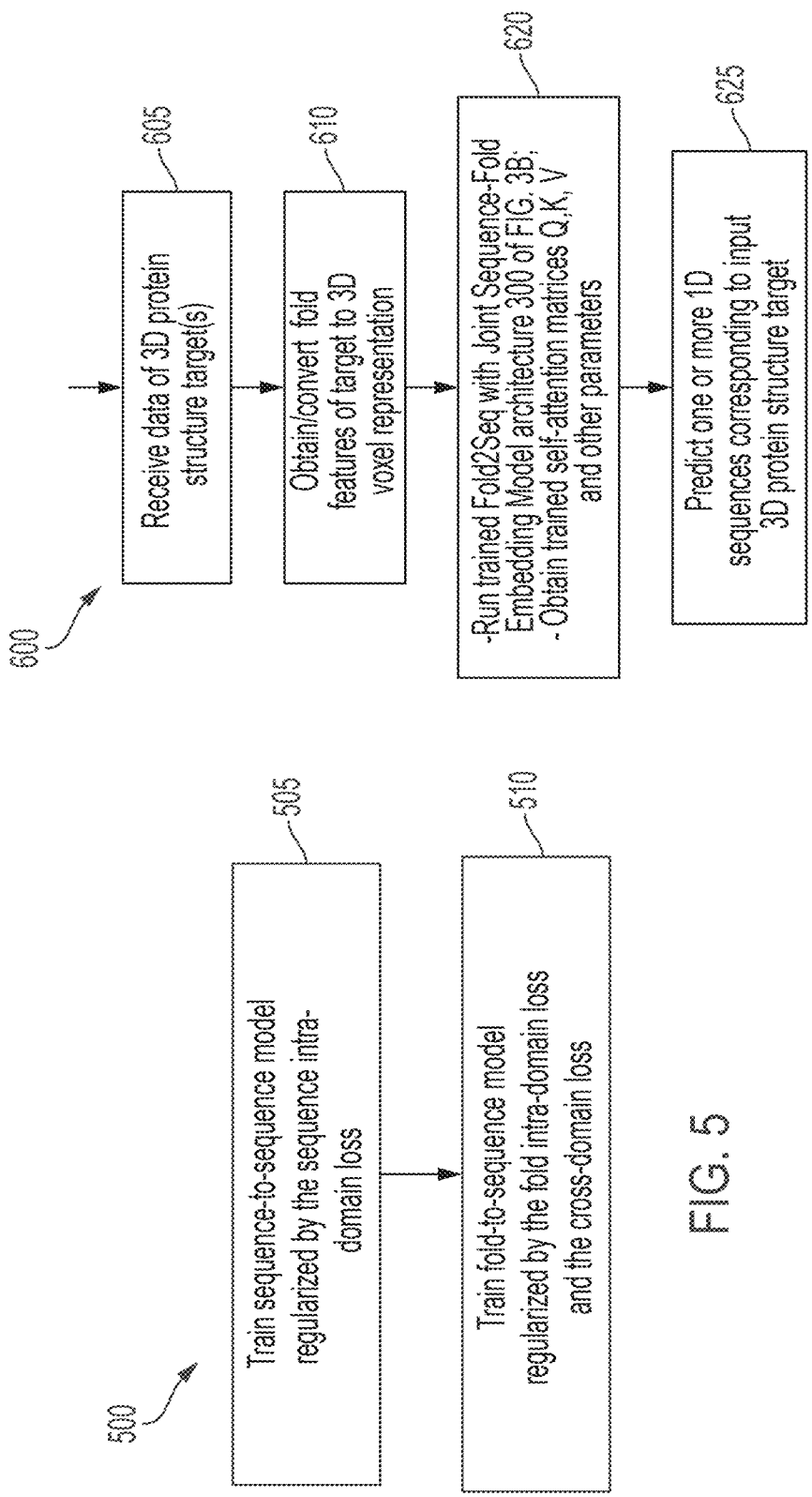

EMBEDDING-BASED GENERATIVE MODEL FOR PROTEIN DESIGN

STATEMENT REGARDING PRIOR DISCLOSURES BY THE INVENTOR OR A JOINT INVENTOR

The following disclosure is being submitted under 35 U.S.C. 102(b)(1)(A): "Fold2Seq: A Joint Sequence (1D)-Fold (3D) Embedding-based Generative Model for Protein Design", Yue Cao, Payel Das, Pin-Yu Chen, Vijil Chenthamarakshan, Igor Melnyk, Yang Shen, International Conference on Learning Representations (ICLR 2021) Sep. 28, 2020 conference submission.

FIELD

The present invention relates to protein engineering generally, and more particularly, to machine-learning systems and methods for designing novel one-dimensional protein sequences consistent with a desired three-dimensional structure or fold.

BACKGROUND

In the biotech field, designing novel protein sequences consistent with a desired 3D structure or fold, often referred to as the "inverse protein folding" problem, is a central, but non-trivial, task in protein engineering. It has a wide range of applications in energy, biomedicine, and materials science. However, challenges exist due to the complex sequence-fold relationship and difficulties associated with modeling 3D folds.

Computational protein design is the conceptual inverse of the protein structure prediction problem, and aims to infer an amino acid sequence that will fold into a given 3D structure. Designing protein sequences that will fold into a desired structure has a broad range of applications, from therapeutics to materials. Despite significant advancements in methodologies as well as in computing power, inverse protein design still remains challenging, primarily due to the vast size of the sequence space- and the difficulty of learning a function that maps from the 3D structure space to the sequence space. Earlier works rely mostly on energy minimization-based approaches, which follow a scoring function (force fields, statistical potentials, or machine learning (ML) models,) and sample both sequence and conformational space. Such methods often suffer from drawbacks such as low accuracy of energy functions or force-fields and low efficiency in sequence and conformational search.

Recently, as the data on both protein sequences (hundreds of millions) and structures (a few hundreds of thousands) is quickly accumulating, data-driven approaches for inverse protein design are rapidly emerging. Generally, data-driven protein design attempts to model the probability distribution over sequences conditioned on the structures: $P(x|y)$, where x and y are protein sequences and structures, respectively. Two key challenges remain: (1) defining a good representation (y) of the protein structure and (2) modeling the sequence generation process conditioned on y.

Despite the recent progress in using ML models for protein design, significant gaps still remain in addressing challenges such as 1) fold representation, and 2) conditional sequence generation. First, the current fold representation methods are either hand-designed, or constrained and do not capture the complete original fold space, resulting in low generalization capacity or efficiency. Second, the sequence encoding and the fold encoding are learned separately in previous methods, which make two latent domains heterogeneous. Such heterogeneity across two domains actually increases the difficulty of learning the complex sequence-fold relationship.

SUMMARY

A system, method and computer program product provides a novel transformer-based generative framework for designing protein sequences conditioned on a specific three-dimensional protein fold.

A system, method and computer program product implementing a model that learns a fold embedding from the density of the secondary structural elements (SSEs) in three-dimensional (3D) voxels, and then models the complex sequence-structure relationship by learning a joint sequence-fold embedding.

In one aspect, there is provided a computer-implemented method to design biological sequences using inverse folding of three dimensional structures. The method comprises: using a first transformer model encoder as part of a sequence-to-sequence model to receive an input one-dimensional biological sequence of nucleotides or amino acids represented as text which correspond with a three-dimensional biological structure, and generate an encoded vector representation of the one-dimensional sequence in a first latent space; using a second transformer model encoder as part of a fold-to-sequence model to receive an encoded representation of a three dimensional biological structure corresponding to the input one-dimensional biological sequence and generate an encoded vector representation of the three dimensional biological structure in a second latent space; and training a transformer model decoder to predict and output an alternative one-dimensional sequence of nucleotides or amino acids based on the encoded vector representations of the one-dimensional sequence and the three dimensional biological structure which will result in a similar three-dimensional biological structure.

In a further aspect, there is provided a computer-implemented system to design biological sequences using inverse folding of three dimensional structures. The system comprises: a memory storage device; and a hardware processor coupled to the memory storage device and configured to perform a method to: use a first transformer model encoder as part of a sequence-to-sequence model to receive an input one-dimensional biological sequence of nucleotides or amino acids represented as text which correspond with a three-dimensional biological structure, and generate an encoded vector representation of the one-dimensional sequence in a first latent space; use a second transformer model encoder as part of a fold-to-sequence model to receive an encoded representation of a three dimensional biological structure corresponding to the input one-dimensional biological sequence and generate an encoded vector representation of the three dimensional biological structure in a second latent space; and train a transformer model decoder to predict and output an alternative one-dimensional sequence of nucleotides or amino acids based on the encoded vector representations of the one-dimensional sequence and the three dimensional biological structure which will result in a similar three-dimensional biological structure.

In a further aspect, there is provided a computer program product for performing operations. The computer program product includes a storage medium readable by a processing circuit and storing instructions run by the processing circuit for running a method. The method is the same as listed above.

BRIEF DESCRIPTION OF THE SEVERAL VIEWS OF THE DRAWINGS

FIG. 5 depicts a method of training the Joint Sequence-Fold Embedding Model architecture of FIG. 3A as a two-stage process;

FIG. 6 depicts an inference methodology 600 in one embodiment using the trained Fold2Seq with Joint Sequence-Fold Embedding Model architecture 300 of FIG. 3B.

DETAILED DESCRIPTION

As known, a protein is formed by a linear chain of amino acids (residues) that defines its one-dimensional (1D) sequence. Chemical nature, as well as physical and chemical interactions with neighboring residues, drive the folding of a sequence into different secondary structure elements or SSEs (i.e., helix, beta-sheet, loop, bend, etc.), that eventually forms a complete native three-dimensional (3D) structure. A protein fold captures the structural consensus of the 3D topology and the composition of secondary structure elements.

In one aspect, the present disclosure provides a system, method and computer program product for solving the inverse protein folding problem, i.e., designing protein sequences conditioned on a protein fold defined as the arrangement (or topology) of the SSEs of the protein relative to each other. A secondary structural element is defined as the three-dimensional (3D) form of local segments of a protein sequence. Protein folds are therefore necessarily based on sets of structural elements that distinguish domains. As protein structure is inherently hierarchical, the complete native structure can have multiple folds and a fold can be present in many protein structures. A single structure (fixed backbone) or an ensemble of structures (flexible backbone) can be used as representatives of a fold. The ensemble representation is also a choice, as it captures the protein dynamics.

In an embodiment, a novel fold representation is presented, through first representing the 3D structure by voxels of the density of the secondary structures elements, and then learning the fold representation through a transformer-based structure encoder. Compared to previous fold representations, this representation has several advantages: first, it preserves the entire spatial information of SSEs. Second, it does not need any pre-defined rules, so that the parameterized fold space is not neither limited nor biased toward any particular fold. Third, the representation can be automatically extracted from a given protein structure. Lastly, the density model also loosens the rigidity of structures so that the structural variation and lack of structural information of the protein is better handled.

In one aspect, a joint sequence-fold embedding learning framework is employed into the transformer-based autoencoder model. By learning a joint latent space between sequences and folds, the model, hereinafter referred to as "Fold2Seq" or "fold-to-sequence", mitigates the heterogeneity between two different domains and is able to better capture the sequence-fold relationship.

Figure 1:
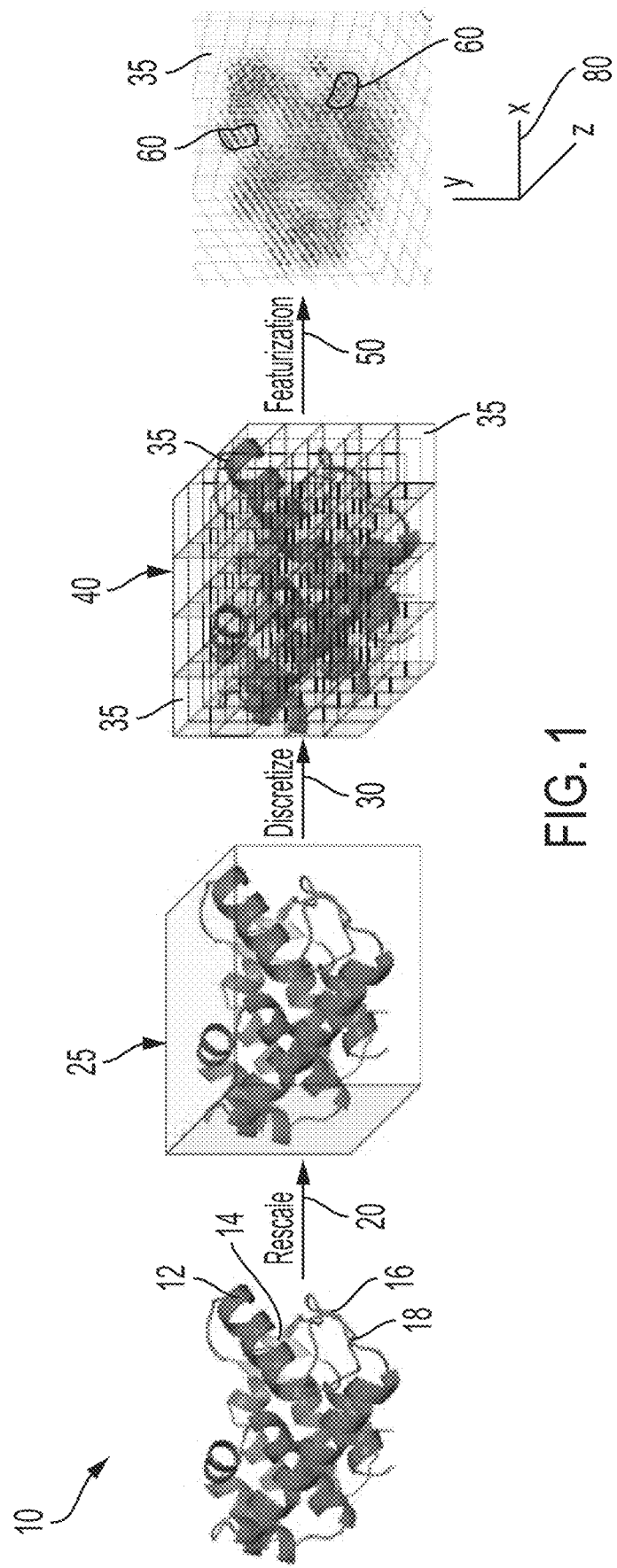
FIG. 1 depicts a 3D representation of an example protein structure to explicitly capture the fold information through three-dimensional (3D) voxels in an example embodiment.

FIG. 1 depicts a three-dimensional (3D) representation of an example protein 3D structure to explicitly capture the fold information and particularly depicts a protein's 3D structural representation through 3D voxels of the density of SSEs. As known, a voxel represents a value on a regular grid in three-dimensional space and is the smallest representation of a 3-D structure. As shown in FIG. 1, there is depicted the structure 10 of a protein T4 LYSOZYME obtained from a protein database enabling search and display of three-dimensional structures of large biological molecules such as the commercially available Protein Data Bank database resource. The secondary structure elements (SSEs) of the protein structure 10 include: helices 12, beta sheets 14, loops 16 and bends/turns 18.

As shown in FIG. 1, to capture the fold representation information of the protein, a size rescaling operation 20 is applied to the protein structure 10 such that the protein 10 is rescaled to fit a 3D voxel grid space or cubic box 25. The cubic box 25 is then subject to discretization process 30 to form a box representation 40 having discretized voxels 35. Then, the voxel/protein structure are subject to featurization 50 to obtain features of each voxel 35 from the protein structure content (i.e., structural elements) within each individual voxel(s). That is, a feature within each voxel is obtained as a probabilistic approximation from its neighborhood. For example, voxel features highlighted as 60 in FIG. 1, are represented in a context dependent way, the context coming from contributions of residues within neighboring voxels. In an embodiment, for each voxel 35, a Gaussian form can be used to decide on the neighboring voxel residue contributions as described with respect to equation 1). For example, an averaging of residue structures 60 is shown present in 3D voxels 35 and its respective neighboring voxels.

More particularly, to represent the protein 3D structure to explicitly capture the fold information, the method includes denoting the position (i.e., a 3D coordinate) of each residue by its alpha carbon. For a given protein with length N, the method first translates the structure to match its center of mass with the origin of the 3D coordinate system, e.g., a Cartesian coordinate system defined by x, y, z axes 80. Then the protein is rotated around the origin to let the first residue be on the negative side of the z-axis. The resulting residue coordinates are represented as $c_1, c_2, \ldots, c_N$.

The secondary structure label is assigned to each residue based on their SSE assignment as provided in the Protein Data Bank. Four types of secondary structure labels are considered: i.e., helix, beta strand, loop and bend/turn. As shown in FIG. 1, in order to consider the distribution of different secondary structure labels in the 3D space, the 3D space 25 is discretized into voxels 35. By only considering the arrangement of SSEs, not their exact coordinates, the original structure is rescaled, so that it fits into a fixed-size cubic box 25. Based on the distribution of sizes of single-chain proteins in the CATH/Gene3D (v4.3) database, e.g., a 40 Å×40 Å×40 Å box is chosen with each voxel of size 2 Å×2 Å×2 Å. The scaling ratio is denoted as r∈ $R^3$. For voxel i, the coordinates of its center are denoted as $v_i$. It is assumed that the contribution of residues j to voxel i follows the Gaussian form according to equation 1) as follows:

$$y_{i,j} = \exp\left(-\frac{\|c_j \odot r - v_i\|_2^2}{\sigma^2}\right) \cdot t_j \quad 1)$$

where $c_i$ is the coordinate of the residue (amino acid) j, σ is the standard deviation of the Gaussian distribution, and $t_j \in \{0, 1\}^4$ is the one-hot encoding of the secondary structure label of amino acid j (e.g., helix, beta strand, loop and bend/turn). The standard deviation of the Gaussian distribution is chosen to be 2 Å, All residues are summed together to obtain the final features of the voxel i:

$$y_i = \Sigma_{j=1}^N y_{i,j}.$$

The fold representation (also referred to as structure representation) y is the vector of $y_i$'s over all voxels i. This fold representation better captures high-level topological parameters that describe a specific fold and results into generated sequences that explore the available sequence space to a specific fold more widely.

As will be described, a "Fold2Seq" framework runs method steps including the encoding of the fold representation y into the latent space and training a Fold2Seq transformer model to learn a joint sequence-fold embedding in order for generating sequences consistent with a desired 3D structure.

Figure 3A:
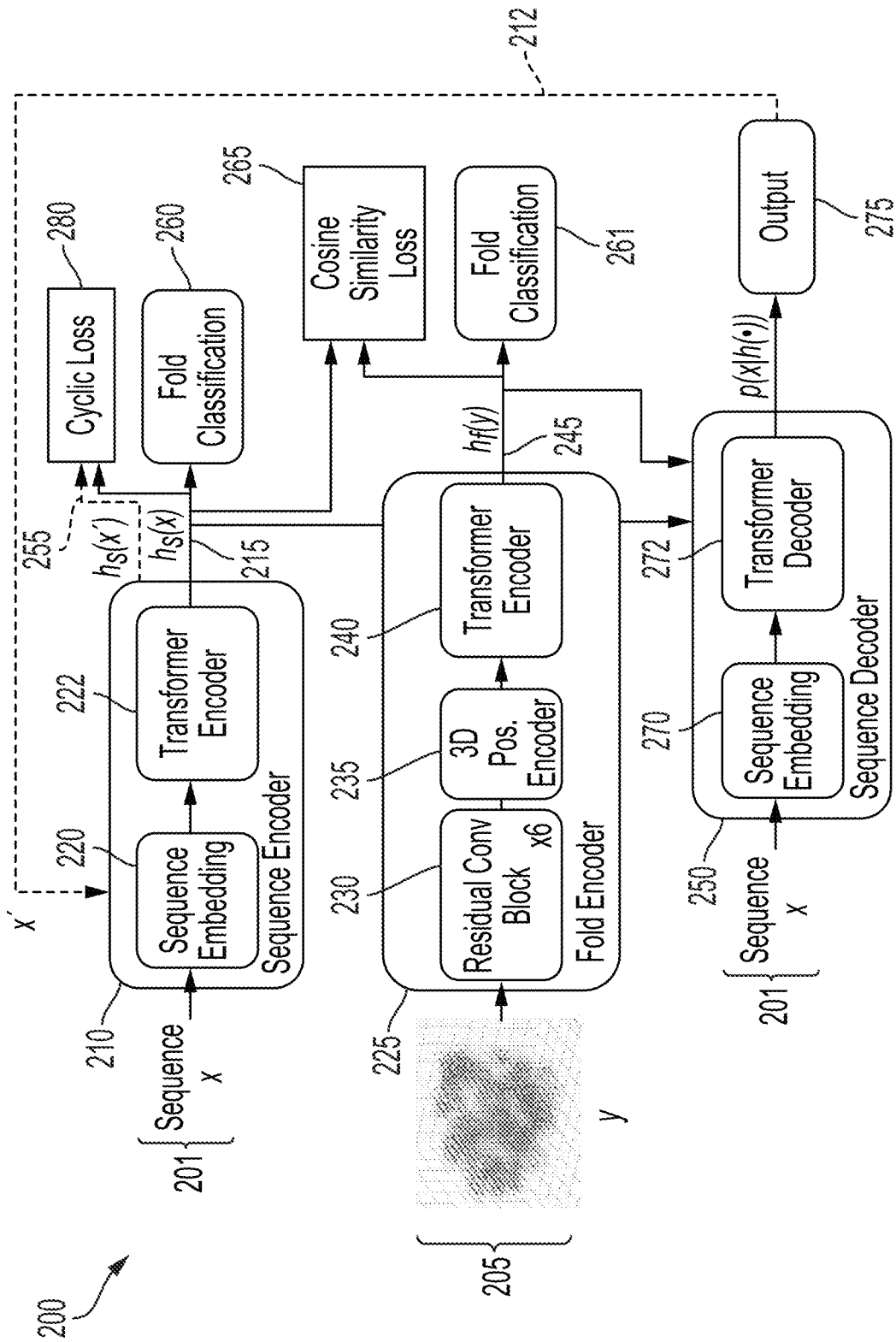
FIG. 3A depicts the Fold2Seq with Joint Sequence-Fold Embedding Model architecture implemented during the model training stage.

FIG. 3A depicts the Fold2Seq with Joint Sequence-Fold Embedding Model architecture 200 implemented during the model training stage.

As shown in FIG. 3A, in the training stage, the transformer model includes three major components: a sequence encoder 210 including a transformer encoder model 222 for generating a latent sequence representation: $h_s(\cdot)$ 215, a fold encoder (also referred to as structure encoder) 225 including a transformer encoder 240 generating a latent fold representation: $h_f(\cdot)$ 245 and a sequence decoder 250 including a transformer decoder 272 for generating an output sequence of symbols 275: $p(x|h(\cdot))$ representing a protein sequence. Both sequence encoder 210 and sequence decoder 250 are implemented using a transformer model. The sequence encoder 210 receives an input one-dimensional ASCII string representation of a protein sequence "x" 201 (or a sequence portion) at a sequence embedding component 220, and the output of the sequence embedding component 220 is input to the transformer encoder 222 that generates encoded sequence $h_s(x)$. As will be explained, the broken arrow 212 input to the sequence encoder 210 and a corresponding broken arrow 255 output of the encoder 210 represent the process for obtaining a cyclic loss value at cyclic loss block 280. The sequence decoder 250 implemented using the transformer model architecture 200 receives the same or similar input protein sequence representation "x" 201 at a sequence embedding component 270, and the output of the sequence embedding component 270 is input to the transformer decoder 272 that generates the output sequence of symbols 275.

As further shown in FIG. 3A, in an embodiment, the sequence encoder 210 and sequence decoder 250 of transformer encode-decode model architecture 200 can be independently trained with just sequence data x, i.e., 1-Dimensional ASCII text representing proteins, without need for parallel input of the corresponding 3D structures of the sequences. In this embodiment, the transformer encoder-decoder architecture is trained in the sequence domain to generate the "sequence2sequence" model. The losses evaluated in this training are reconstruction losses and fold classification loss.

Further, with the sequence encoder 210 frozen, the fold encoder 225 and sequence decoder 250 of the transformer encode-decode model architecture 200 are trained in parallel with the fold encoder 225 receiving 3D protein features "y" 205 of the 3D voxels for known 3D structures in the training data set and the sequence decoder 250 receiving as input the corresponding "ground truth" 1D protein sequences x corresponding to the 3D protein features "y" 205 of the 3D voxels being trained. As explained in greater detail, the losses evaluated in this structure domain training are reconstruction losses, fold classification loss and further, cyclic losses and cosine similarity loss.

In both independent training and parallel training embodiments, the input sequence to the sequence encoder 210 is subject to sequence embedding, e.g., a predefined input piece or portion (one or more residues or amino acids) of the protein sequence is converted into a vector representation.

Further, in the parallel training embodiment, the corresponding voxel input fold representation features "y" are received at residual conversion block 230. In an embodiment, the fold encoder 225 of the model architecture includes six (6) residual conversion blocks 230 followed by a 3D positional encoder 235. Each residual block is a deep neural network (DNN) and can have, for example, two 3D-convolutional layers (3×3×3) and batch normalization layers for use in transforming the input into a multi-dimensional vector. The 3D positional encoder 235 is a 3D extension of the sinusoidal encoding described in the commonly implemented transformer encoder model of FIG. 4 (e.g., found in Vaswani et al., entitled "Attention is all you need" in Advances in Neural Information Processing Systems, pp. 5998-6008, 2017) where a vector that represents a position is added to the input embeddings at the bottom of the encoder/decoder stack.

In an embodiment, an extension of the sinusoidal encoding used in a commonly implemented transformer model is used to encode each position in fold encoder 225 as follows:

$PE(x,y,z,2i)=\sin(x/10000^{2i/h})+\sin(y/10000^{2i/h})+\sin(z/10000^{2i/h})$ $PE(x,y,z,2i+1)=\cos(x/10000^{2i/h})+\cos(y/10000^{2i/h})+\cos(z/10000^{2i/h})$ where x, y and z are the respective coordinates/positioning of the residue in a voxel with respect to x, y, z axes in the 3D graphic space, i is the size or dimension of the sequence and h is the model dimension.

After the positional encoding, the 3D vector is flattened to be 1D and is provided as the input of a transformer encoder 240. In an embodiment, the length of the transformer model input is fixed to be $l_f=5^3=125$. The output 245 of the transformer fold encoder 225: $h_f(y)$, is the latent fold representation of y.

In an embodiment, a fold-to-sequence reconstruction loss 275 is based on the auto-encoder model:

$RE_f=p(x|h_f(y)).$

However, training based on $RE_f$ alone can suffer due to the heterogeneity of x and y. To overcome this challenge, the Fold2Seq framework method encodes the sequence x through the sequence encoder 210 into the latent space as: $h_s(x)$, to generate output 215 of the transformed sequence encoder which is the latent sequence representation of x. This is done through a simple sequence-to-sequence reconstruction loss: $REs=p(x|h_s(x))$ output 275 of sequence decoder 250. Then, a joint latent space is learned between $h_f(y)$ and $h_s(x)$ through a novel sequence-fold embedding learning framework.

Joint Embedding Learning

Figure 2:
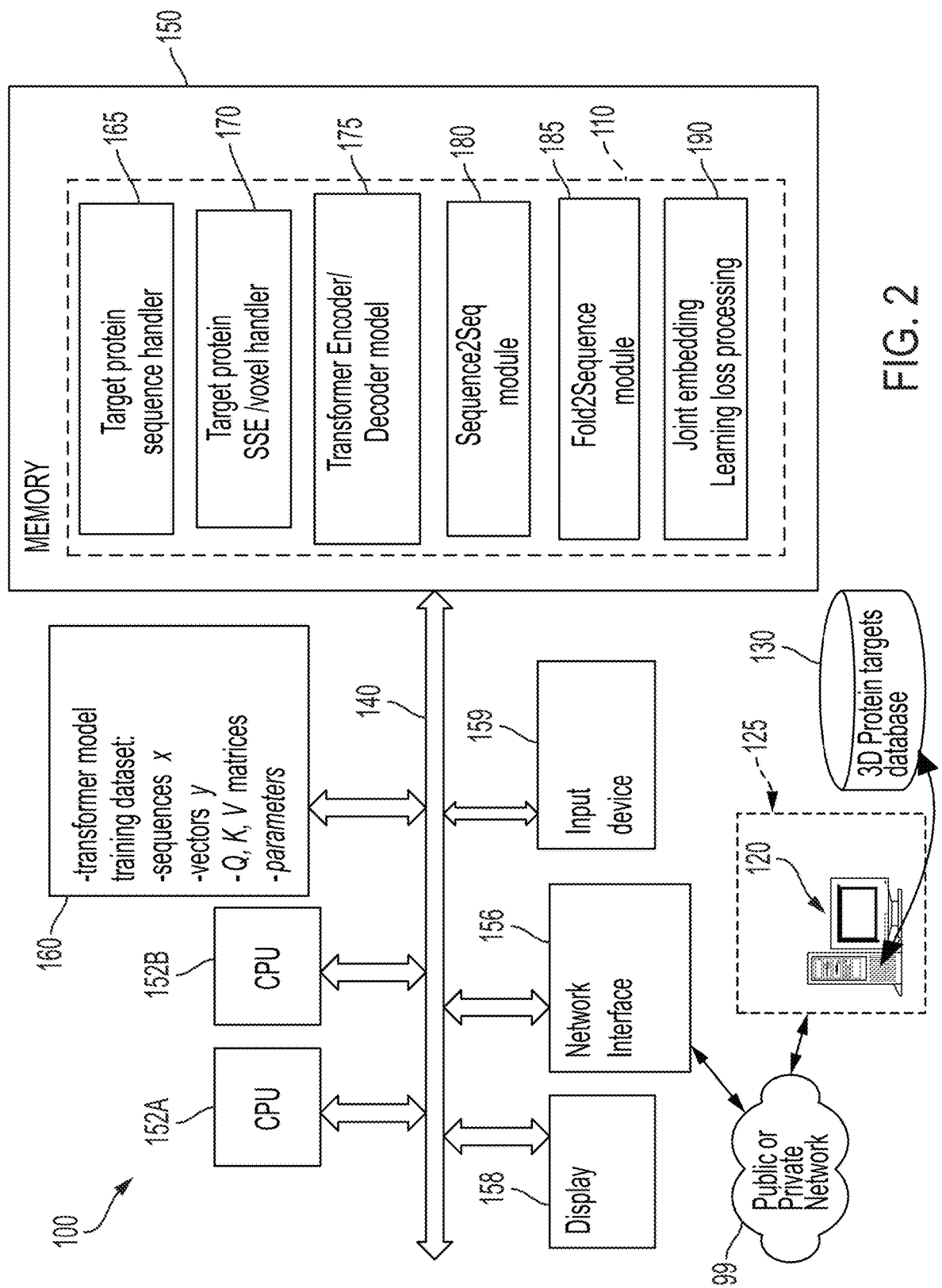
FIG. 2 schematically shows an exemplary computer system/computing device which is applicable to implement the embodiments for predicting one-dimensional protein sequences from target three-dimensional protein structures.

To learn a joint latent space between $h_f(y)$ and $h_s(x)$ a novel sequence-fold embedding learning framework is implemented using the transformer model of FIG. 2.

Typically, learning a joint embedding across two domains needs two intra-domain losses and one cross-domain loss. An intra-domain loss forces two semantically similar samples from the same domain to be close to each other in the latent space, while a cross-domain loss forces two semantically similar samples in different domains to be closer.

As referred to herein, 'semantically similar' means that the proteins should have the same fold(s). Therefore, the method run in model architecture 200 implements a supervised learning task for learning intra-domain similarity as depicted by fold classification blocks 260, 261. Specifically, the outputs of both encoders: $h_f(y) \in R^{l_f \times d}$ and $h_s(x) \in R^{l_s \times d}$ will be averaged along $l_f$ and $l_s$ dimensions, followed by a MLP+softmax layer to perform fold classification at blocks 260, 261 in FIG. 2), where $l_s$, $l_f$ and d are the length of the sequence, the fold and the latent state, respectively. The two MLP layers' parameters are shared. The category labels are one-hot encoded and follow the fold (topology) level of hierarchical protein structure classification in a CATH 4.2 dataset. This results in the generating of two intra-domain losses: $FC_f$ and $FC_s$, the cross entropy losses of fold classification from $h_f(y)$ and $h_s(x)$ respectively. The benefits of these two classification tasks are as follows: First, the fold encoder 225 is forced to learn the fold representation. Second, as the same supervised learning task is performed on the latent vectors 215, 245 from two domains, it will not only learn the intra-domain similarity, but also cross-domain similarity. However, without explicit cross-domain learning, the two latent vectors $h_f(y)$ 245 and $h_s(x)$ 215 could still have minimal alignment between them.

In the transformer sequence decoder 250, each element in the non-self attention matrix is calculated by the cosine similarity between the latent vectors from the encoder 210 and the decoder 250, respectively. In an embodiment, the cosine similarity block 265 in FIG. 3A computes and maximizes a cosine similarity between $h_f(y) \in R^{l_f \times d}$ and $h_s(x) \in R^{l_s \times d}$ as the cross-domain loss. In the method, there if first calculated the matrix-product (dot product) between $h_f(y)$ and $h_s(x)$ as a similarity matrix $Q = h_f(y) \cdot h_s(x)^T$, $Q \in R^{l_f \times l_s}$.

The $i^{th}$ row in similarity matrix Q represents the similarity between $i^{th}$ position in the fold and every position of the sequence. The method run in model architecture 200 is configured to find the best-matching sequence piece with each position in the fold (i.e., maximize similarity between the sequence embedding and structure embedding for the same sequence and structure). To achieve this, the similarity matrix Q first goes through a row-wise average pooling with kernel size k, followed by the row-wise max operation according to equation 2) as follows:

$$q = _{row}\!max(AvgPool_{row}^k(Q)), q \in R^{l_f \times 1} \qquad 2)$$

where row means the operation is a row-wise operation. In an example implementation, k is chosen as k=3, which means the scores of every 3 continuous positions in the sequence will be averaged. A final average over all positions in the fold is performed to obtain the final similarity score:

$$CS = mean(q).$$

Besides the cosine similarity loss, model architecture 200 includes a 'Cyclic Loss' block 280 in FIG. 3A to compute and add a cyclic loss as another term of the cross-domain loss. Specifically, the argmax x' 212 of the decoder output 275 of fold-to-sequence model for a current sequence x is computed as:

$$x' = \arg\max p(x|h_f(y)).$$

where $h_f(y)$ is the encoded latent state representation of the fold structure y corresponding to current sequence x. In the method of the model architecture 200, the x' is fedback to the sequence encoder 210 as shown by the dashed line 212 in FIG. 2. The sequence encoder 210 implements embedding methods for generating the cyclic-sequence latent state: $h_s(x')$ 255. The cyclic loss block 280 runs a method for comparing the cyclic-sequence latent state $h_s(x')$ 255 with the native sequence latent state $h_s(x)$ 215 through the square of the L2 distance according to equation 3) as follows:

$$CY = \|h_s(x') - h_s(x)\|_2^2 \qquad 3)$$

To summarize, the complete loss objective is the shown according to equation 4) as follows:

$$L = \lambda_1 RE_f + \lambda_2 RE_s + \lambda_3 FC_f + \lambda_4 FCs + \lambda_5 (CY - CS) \qquad 4)$$

where $\lambda_1$ through $\lambda_5$ are the hyperparameters for controlling the importance of these losses.

Figure 3B:
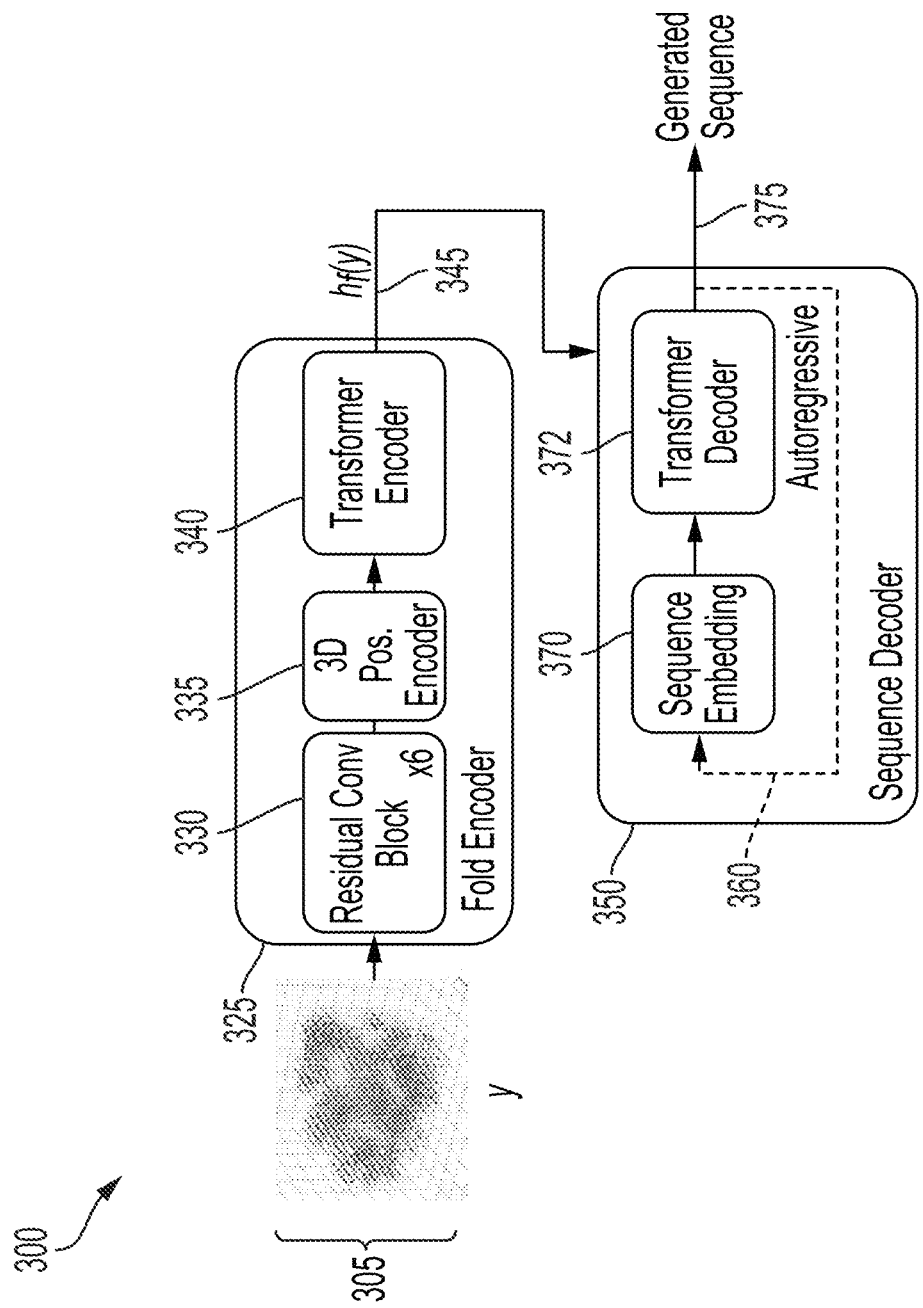
FIG. 3B depicts the Fold2Seq with Joint Sequence-Fold Embedding Model used during inference.
Figure 4:
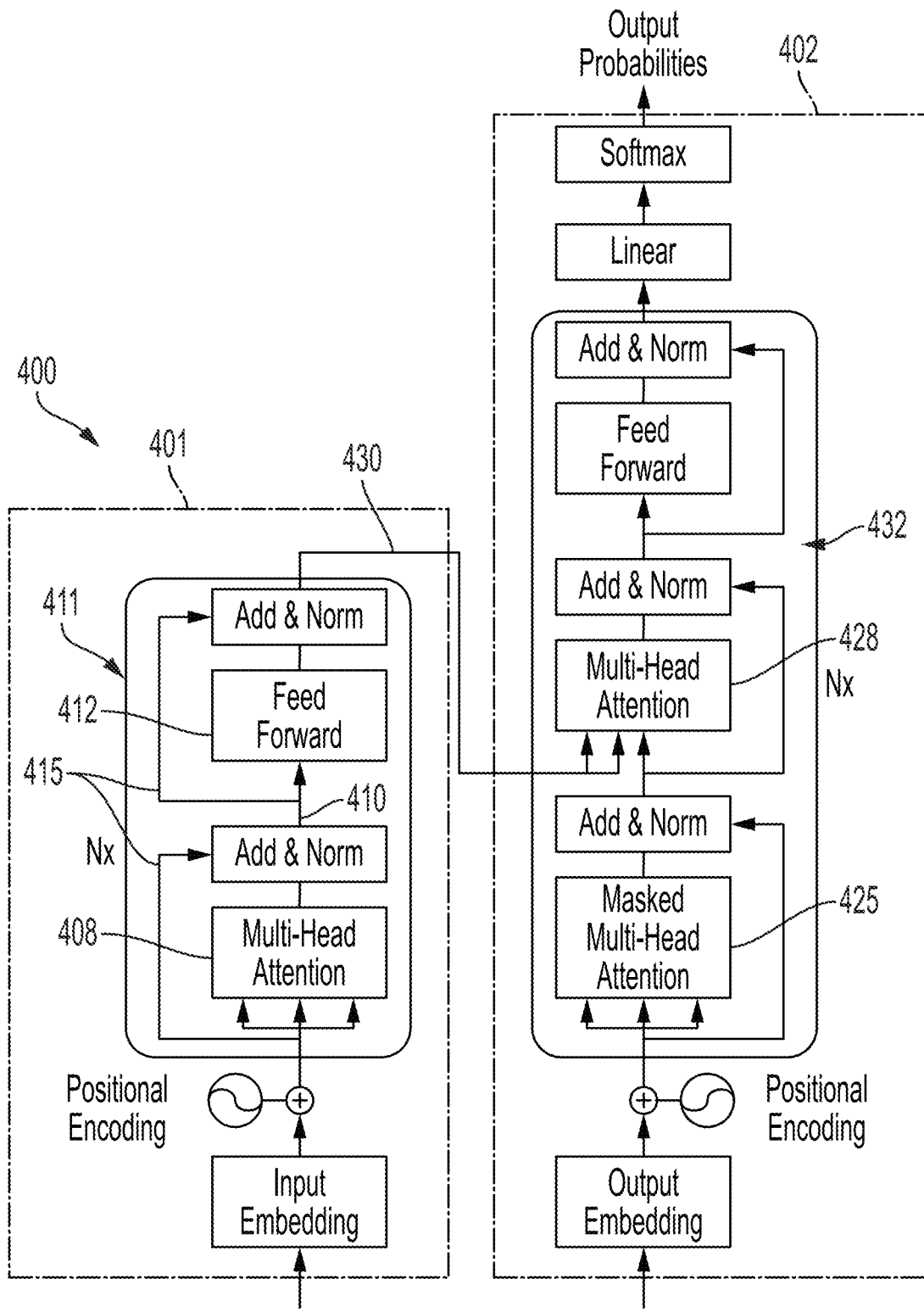
FIG. 4 illustrates an example of a Transformer that may use the techniques disclosed herein according to certain embodiments.

FIG. 4 illustrates a non-limiting example of a transformer architecture 400 according to Vaswani et al., that can function as the sequence encoder and sequence decoder functions according to embodiments of FIGS. 3A, 3B. Alternatively, other types of encoder-decode architectures can be implemented besides a transformer model.

In FIG. 4, transformer 400 includes an encoder 401 and a decoder 402. Encoder 401 may include a stack of N layers 411. Each layer 411 may include two sub-layers that perform matrix multiplications and element-wise transformations. The first sub-layer 408 may include a multi-head self-attention network, and the second sub-layer 412 may include a position-wise fully connected feed-forward network.

As shown in FIG. 4, embedded input vectors first flow through the encoder's multi-headed self-attention layer 408 that enables the encoder to look at other residues/portions in the input sequence as it encodes a specific input sequence portion (e.g., an amino acid). The outputs 410 of the self-attention layer are fed to a feed-forward neural network 412. The exact same feed-forward network is independently applied to each position. The decoder has both those layers, but between them is an attention layer 428 that helps the decoder 402 focus on relevant parts of the input sequence.

In embodiments, each piece/residue (e.g., one or more amino acids) of an input sequence at a particular position flows through its own path in the encoder. There are dependencies between these paths in the multi-headed self-attention layer 408. The feed-forward layer does not have those dependencies, however, and thus the various paths can be executed in parallel while flowing through the feed-forward layer 411.

The encoder 401 processes a list of input vectors by passing these vectors into the multi-headed self-attention layer 408, then into a feed-forward neural network, and the generated output is sent upwards to the next encoder layer of the Nx layers.

As the model processes each vector (corresponding to a piece/residue of the input protein sequence x at a particular position of the input sequence), the 'self attention' layer 408 allows the model to look at other positions/residues in the input sequence to better encode that particular position of the input sequence x.

As further shown in FIG. 4, a residual connection 415 may be used around each of the two sub-layers, followed by layer normalization where the residual connection adds the input to the output of the sub-layer. Layer normalization is a normalization method for standardizing the inputs to a layer to effect stabilizing the learning process and reduce the number of training epochs required to train the network. The output of each sub-layer may be written as LayerNorm(x+Sublayer(x)), where Sublayer(x) is the function implemented by the sub-layer. In the encoder phase, the Transformer encoder 401 receives successive pieces or residues of the input amino acid chain x for the input protein being processed and converts each respective successive piece into an input embedding vector of a defined dimension. To maintain the order of the successive input tokens representing the successive amino acids within the sequence x, positional information of the input piece in the form of a positional encoding vector of the same dimension is added to the embedding vector in the manner described hereinabove. That is, the transformer adds a vector to each input embedding. These vectors follow a specific pattern that the model learns, which helps it determine the position of each sequence piece, or the distance between different pieces in the sequence. In an embodiment, this positional encoding can include use of sine and cosine functions of different frequencies.

After generating an embedding with added position encoding vector for each piece in the input sequence x, transformer encoder employs the attention function to perform the mapping of a query and a set of key-value pairs to an output, where the query, keys, values, and output are all vectors. The added positional values to the embeddings provides meaningful distances between the embedding vectors once they're projected into Query/Key/Value (Q, K, V) vectors used during self-attention.

As further shown in FIG. 4, transformer decoder 402 may also include a stack of N layers 432. In addition to the two sub-layers in each encoder layer 411, each layer 432 in decoder 402 can include a third sub-layer that performs multi-head attention over the output 430 of the encoder stack. In an embodiment, output of the encoder stack include the native sequence latent state $h_s(x)$ and latent space fold representation $h_f(y)$ and loss is computed after passing these inputs through the decoder. Similar to layers 408, 411 in encoder 401, residual connections around each of the sub-layers may be used in layers 432 in decoder 402, followed by layer normalization. One self-attention sub-layer in the decoder stack is modified to form a "masked multi-head attention" layer 425 to mask inputs to the decoder from future time steps and prevent positions from attending to subsequent positions. The masking, combined with offsetting the output embeddings by one position, ensures that the predictions for a position i can depend only on the known outputs at positions less than i. Decoder 402 may generate one piece of a protein sequence at a time. The first piece generated at a layer may be based on the final representation of the encoder (e.g., offset by 1 position). Every protein sequence piece predicted subsequently may attend to the previously generated pieces at that layer of the decoder and the final representation of the encoder.

For each input portion (e.g., residue or amino acid) of input sequence x, self-attention aggregates information from all other pieces in the context of the input sequence to create a new representation for each piece that takes into account all other pieces/portions in the sequence. This process can be repeated for multiple times in a sequence to successively build newer representations on top of previous ones.

To calculate self-attention, there is created three vectors from each of the encoder's input vectors (e.g., the embedding vectors of each successive sequence piece/residue). For each sequence portion, there is created a respective Query vector, a Key vector, and a Value vector by multiplying the embedding by respective three matrices that are trained during the training process. The Query vector q encodes the piece/position that is paying attention, and the Key vector k encodes the piece/position to which attention is being paid. The key vector k and the query vector q together determine the attention score between the respective pieces/positions. The output is computed as a weighted sum of values, where the weight assigned to each value is computed by a compatibility function of the query with the corresponding key.

The use of self-attention further requires the calculation of a score for each other position of the input sequence against the sequence portion at a certain position currently being encoded. The score determines how much focus to place on other parts of the input sequence as a current sequence portion at a certain position is being encoded. In an embodiment, the score is calculated by taking the dot product of the query vector with the key vector of the respective portion of the sequence at the position being scored. Remaining steps perform dividing the scores by a number to produce more stable gradients. This number can be equal to the square root of the dimension of the key vectors used. This result is then passed through a Softmax operation that normalizes the scores so they're all positive and add up to 1. The softmax score is used to determine how much each sequence portion will be expressed at this position.

Further steps include multiplying each value vector by the softmax score (in preparation to sum them up) and to sum up the weighted value vectors. This produces the output of the self-attention layer for the embedded vector of the input protein sequence portion at this current position.

These self-attention calculations can be performed using matrices such that an 'embedding' matrix is formed where every row in the embedding matrix is packed with a corresponding different sub-portion or position of the input protein sequence. The method calculates the Query, Key, and Value matrices which are then multiplied with the packed embedding matrix.

A computation of the scaled dot-product attention on a set of queries can be performed according to:

$$\text{Attention}(Q, K, V) = \text{softmax}\left(\frac{QK^T}{\sqrt{d_k}}\right)V$$

where Q is the matrix of queries packed together, K and V are the matrices of keys and values packed together, and $$\frac{1}{\sqrt{d_k}}$$

is the scaling factor.

To learn diverse representations, multi-head attention applies different linear transformations to the values, keys, and queries for each of multiple attention heads, where different weight matrices may be used for the multiple attention heads and the results of the multiple attention heads may be concatenated together.

As the self-attention layer is "multi-headed", the attention layer is able to focus on different positions such as where protein folds are represented as it gives the attention layer multiple "representation subspaces" which are represented by multiple sets of Query/Key/Value weight matrices. Each of these sets is randomly initialized. Then, after training, each set is used to project the input embeddings (or vectors from lower encoders/decoders) into a different representation subspace. Thus, with multi-headed attention, separate Q/K/V weight matrices are maintained for each head resulting in different Q/K/V matrices which can be multiplied by the input embedding matrix to produce the Q/K/V matrices. These multiple matrices can be condensed down into a single matrix for input processing by the next feed-forward layer. For example, all of the attention heads (matrices) can be concatenated and then multiplied by an additional weights matrix that is trained jointly with the model and results in a single matrix that captures information from all of the attention heads to produce the output the layer 408 that is input to the feedforward layer 411.

Multi-head attention allows the framework to jointly attend to information from different representation subspaces at different positions. The multi-head attention may be performed using a tensor operation, which may be split into multiple sub-operations (e.g., one for each head) and performed in parallel by multiple computing engines as described herein.

That is, instead of performing a single attention function with $d_{model}$-dimensional keys, values and queries, the queries, keys and values are linearly projected h times with different, learned linear projections to $d_k$, $d_k$ and $d_v$ dimensions, respectively. On each of these projected versions of queries, keys and values, the attention functions are then performed in parallel, yielding dv-dimensional output values. These are concatenated and once again projected, resulting in the final values.

Multi-head attention allows the model to jointly attend to information from different representation subspaces at different positions.

$$\text{MultiHead}(Q,K,V)=\text{Concat}(\text{head}_1, \ldots, \text{head}_h)W^O$$

where $\text{head}_i = \text{Attention}(QW_i^Q, KW_i^K, VW_i^V)$
where the projections are parameter matrices $W_i^Q \in \mathbb{R}^{d_{model} \times d_k}$, $W_i^K \in \mathbb{R}^{d_{model} \times d_k}$, $W_i^V \in \mathbb{R}^{d_{model} \times d_v}$ and $W^O \in \mathbb{R}^{hd_v \times d_{model}}$.

In an example implementation, the system can employ h=8 parallel attention layers, or heads. For each of these, $d_k=d_v=d_{model}=h=64$. Due to the reduced dimension of each head, the total computational cost is similar to that of single-head attention with full dimensionality.

Training Scheme

FIG. 5 depicts a training and decoding methodology in one embodiment. In the model training methodology, rather than training the sequence encoder 210 and the fold encoder 225 together, a two-stage training strategy is implemented as shown in the method 500 of FIG. 5. In the first stage, at 505, there is trained the sequence-to-sequence model regularized by a sequence intra-domain loss L1, where $L_1=\lambda_2 RE_s + \lambda_2 FC_s$. In this scheme, an independent training of the sequence-to-sequence model using sequence encoder 210 for receiving input sequence data x and sequence decoder 250 for receiving corresponding "ground truth" sequences as labels, such that the model can learn a same or one or more alternative 1D sequences of different probabilities corresponding to the input sequence x. That is, the sequence decoder 250 learns to generate identical and/or similar alternative ID ASCII text representations of 1D input protein sequences x 201.

After the first stage is finished in the sequence domain, a second training stage is invoked at 510 for training the fold-to-sequence model regularized by a fold intra-domain loss and a cross-domain loss L2, where $L_2=\lambda_1 RE_f + \lambda_3 FC_f + \lambda_5(CY-CS)$, while keeping the sequence encoder frozen. In this scheme, the fold encoder 225 receives input structures y and sequence decoder 250 receives corresponding "ground truth" sequences (if known) as labels. The model then employs the sequence-fold joint embedding learning framework to teach the model to predict 1D ASCII text representations of the input protein structures (folds) y such that the corresponding output sequences can fold similarly to the input protein structure y represented in three dimensions that is input to the fold encoder block 225 in the manner as shown in FIG. 1. In this case, the model performs a classification in that one protein fold (label) can be one a grouping of multiple different structures and thus, the model is trained to predict which fold a given structure belongs to.

In an embodiment, the training model is implemented using a machine learning framework such as Pytorch (pytorch.org) or similar framework. Each transformer block 210, 225 and 250 has 4 layers and d=256 latent dimensions.

In an embodiment, to increase the robustness of the model for rotated structures, the training data can be augmented by right-hand rotating the each structure by 90°, 180° and 270° along each axis (x, y, z). Given an input protein sequence y, it can be rotated multiple time by various degrees resulting in the x, y and z residue coordinates changing but the relative positioning of them do not change. Thus, the model is trained with each of these rotated variants so it can predict the same sequence x regardless of the orientation/rotation of the input structure y.

As a result, the training data is augmented by 3×3=9 times. A learning rate schedule can be implemented that follows a known transformer model described in Vaswani et al. In an embodiment, the importance parameter $\lambda_5$ is an exponential decay such as $$\lambda_5 = \frac{1}{2}^{\#epoch-e}$$

in the loss function, while $\lambda_1$ through $\lambda_4$ and e are tuned based on the validation set, e.g., $\lambda_1=1.0$, $\lambda_2=1.0$, $\lambda_3=0.02$, $\lambda_4=1.0$, #epoch is number of full passes over the dataset, and e=3. For example, by training the model 200 on 2 Nvidia Tesla K80 GPUs, with batch size 128, up to 200 epochs can be trained in every training stage with an early stopping strategy based on the loss on the validation set.

Inference Scheme

Once the Fold2seq model 300 model is trained, given an input protein structure, the model generates one or more novel 1D protein sequences that fold according to that input protein structure.

As shown in FIG. 3B, during inference, only the trained Fold2seq model 300 of the transformer model architecture 200 is needed for decoding sequences. That is, Fold2Sequence model 300 including the trained fold encoder block 325 and sequence decoder block 350 trained to learn a joint sequence-fold embedding in order for generating sequences consistent with a desired 3D fold structure is used.

FIG. 3B depicts the trained Fold2Seq with Joint Sequence-Fold Embedding Model architecture 300 including a trained fold encoder 325 including a transformer encoder 340 implementing self-attention for generating the latent fold representation: $h_f(y)$ 345, and the trained sequence decoder 350 including a sequence embedding component 370 and a transformer decoder component 372 implementing masked self-attention that receives the latent fold representation $h_f(y)$ 345 and processes the latent fold representation $h_f(y)$ for generating an output sequence of symbols 375 representing a protein sequence that can fold according to a desired input 3D protein structure.

As shown in FIG. 3B, the trained fold encoder 325 receives 3D voxel features representation "y" 305 of a fold/structure of a desired or target protein, RNA or DNA molecule, for which a corresponding 1D nucleotide or amino acid sequence 375 is to be predicted that will fold according to such input structure. The features representation "y" are input as a vector sequence where all target protein residues at a voxel is a summation of the final features of the voxel i, i.e., $y_i = \Sigma_{j=1}^{N} y_{i,j}$. In particular, the input fold representation y 305 is the vector of $y_i$'s over all voxels that is input to residual conversion block 330. In an embodiment, the fold encoder 325 of the Fold2seq model 300 includes six (6) residual conversion blocks 330 followed by a 3D positional encoder 335 in the manner as described in connection with training of the model 200. Each residual block is a deep neural network (DNN) and can have, for example, two 3D-convolutional layers (3×3×3) and batch normalization layers. The 3D positional encoder 335 is a 3D extension of the sinusoidal encoding described in connection with the training of the transformer encoder model 200.

After the positional encoding at 3D positional encoder 335, the 3D vector is flattened to be ID and is provided as the input of the transformer encoder 340 to generate the output latent fold representation $h_f(y)$ 345. The output latent fold representation of y, i.e., $h_f(y)$ 345, is input to the transformer decoder block 350 where trained sequence embedding component 370 and transformer decoder 372 are programmed to generate the output sequence of symbols 375, i.e., a ID ASCII text representation of the input target protein structure representation y. At each step, the model is autoregressive in that previously generated symbols of prior sequence portions are consumed as additional input 360 when generating a symbol of a next sequence portion. That is, in the autoregressive method, P(x|y) is decomposed through the chain rule: $P(x|y) = \cup_{i=1}^{n} P(x_i | x_1, x_2, \ldots, x_{i-1}, y)$, where $x = (x_1, x_2, \ldots, x_n)$.

In one embodiment, a top-k sampling strategy is used for sequence generation, e.g., where k is set to be 5 (tuned based on a validation set).

As an example, it is conceivable that a protein structure y (e.g., a new protein structure designed for a particular function) is input with a little or no knowledge of how the corresponding 1-D amino acid sequence should like. In this scenario, the Fold2Seq model output will be one sequence or several alternate sequences that can potentially fold into such structure. Alternately, if there is little knowledge of how the sequence should look (i.e., low resolution structures), the Fold2Seq model has learned from the fold information of known structures how to output sequences that can potentially fold into such structure.

The 3D voxel representation and the joint embedding learning framework, which includes intra-domain and cyclic losses, embodied as Fold2Seq model architecture of FIG. 3B, results in a significant performance improvement. FIG. 6 depicts an inference methodology 600 in one embodiment using the trained Fold2Seq with Joint Sequence-Fold Embedding Model architecture 300 of FIG. 3B. In a first step 605, the trained fold encoder 310 receives as input a 3D representation y of a desired fold or structure of a protein. In embodiments, the input can comprise a low-resolution protein structure y, an ensemble of protein structures and/or a protein structure that is incomplete and missing a percentage of residues and which may or may not exist any corresponding known ground truth sequence. At 610, the steps can be performed to obtain and/or convert the representation into a vector corresponding to a 3D voxel representation. That is, the input 3D structure is rescaled to fit a 3D voxel grid space which is then discretized, and then subject to featurization to obtain features of each voxel 35 from the protein's structural elements (i.e., a probabilistic approximation from its neighborhood). Step 610 results in the output target protein residues (amino acid) j at each voxel computed as a summation of the final features of the voxel i, i.e., $y_i = \Sigma_{j>1}^{N} y_{i,j}$. Then, at 620, the method retrieves the parameters and Q, K, V matrices obtained for the multi-headed self-attention layer processing during training of the Fold2Seq with Joint Sequence-Fold Embedding Model and the model is run to output the corresponding 1D sequence at 625.

The Fold2Seq model framework 200 runs systems and methods that demonstrably exhibit superior performance on perplexity, native sequence recovery rate, diversity and native structure recovery accuracy, when compared to competing methods including the state-of-the-art RosettaDesign and other neural net models. Experiments on real-world test sets further demonstrates the unique practical utility and versatility of Fold2Seq model compared to the structure-based baselines. Thus, the Fold2Seq model can benefit anyone engaged in 3D structure-controlled protein sequence design for Antibody/Vaccine Discovery, Enzyme/Biocatalyst Design, and beyond (e.g., Engineered polymers and biomaterials). The Fold2Seq model framework is readily applicable to any sequence design problem that can be represented as a text string and has a known 3D template, can handle availability of more than one (similar) structural templates, and further, can accommodate any additional labels/constraints (stability, function, etc.).

Figure 7:
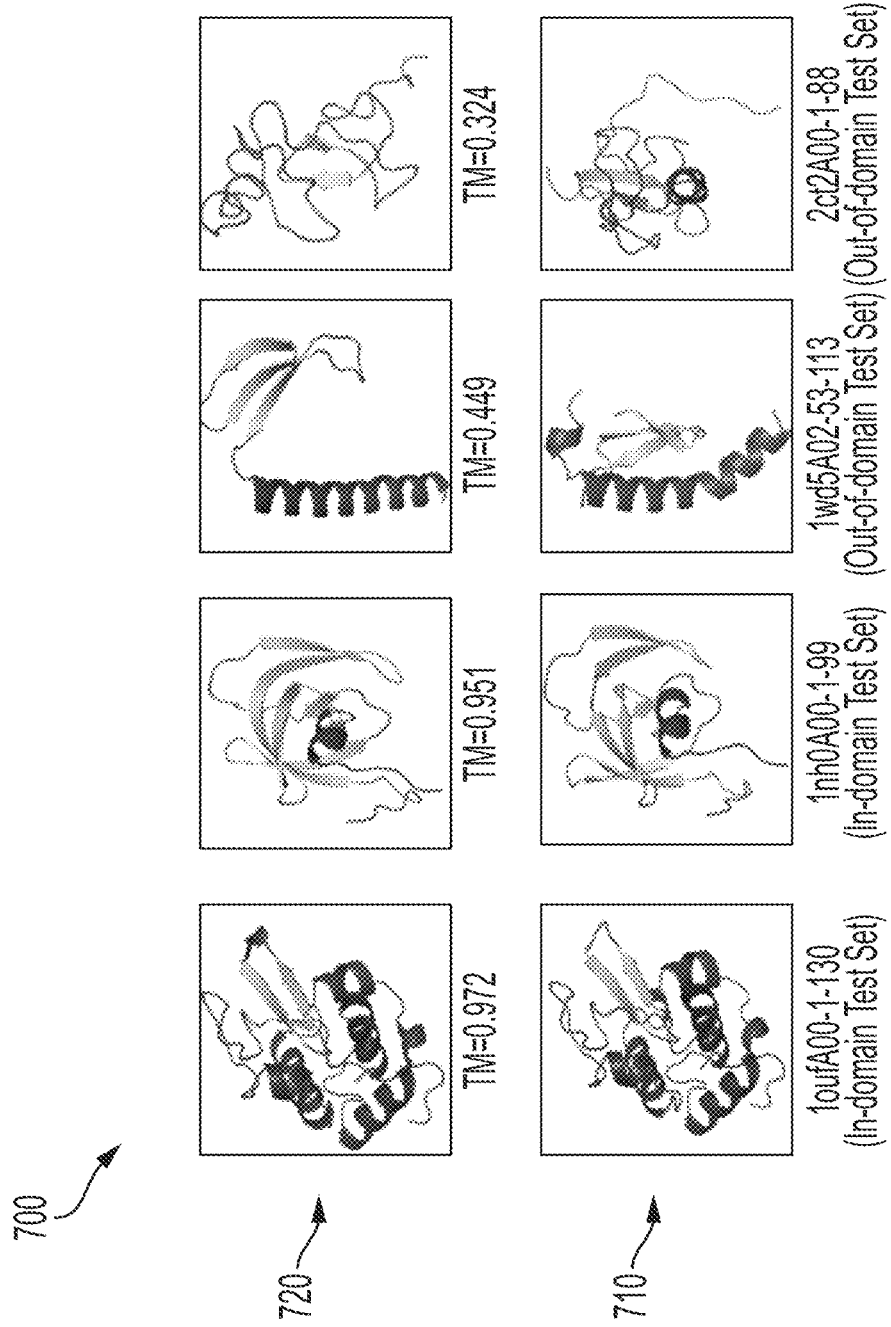
FIG. 7 depicts a comparison of "ground truth" protein structures and their corresponding resulting structures designed in accordance with the respective sequences obtained from the model architecture of FIG. 3B.

FIG. 7 depicts a comparison 700 of several native or "ground truth" protein structures 710 and their corresponding resulting structures 720 designed in accordance with the respective 1D sequences obtained from outputs of running the Fold2Seq with Joint Sequence-Fold Embedding Model architecture 300 of FIG. 3B. As shown in FIG. 7, the resulting folded structures 710 are very similar to their ground truth structures and the Fold2Seq model performs better than prior art methods for the respective input 3D structures. The identifiers indicated at the bottom are the CATH domain names of each structure (see e.g., cathdb.info). Fold2Seq is also able to capture the diversity of sequences within a fold.

In embodiments, the Fold2Seq model architecture of FIG. 3B can be used to perform design tasks conditioned on: (1) Low-resolution structures; (2) Structures with region of missing residues; and (3) nuclear magnetic resonance (NMR) ensembles.

With respect to use of the Fold2Seq model architecture of FIG. 3B to design Low-resolution structures, a method first requires creating a low-resolution structure dataset from a protein structures data source, e.g., Protein Data Bank. In an embodiment, the protein structures data source contains low resolution proteins (single-chain), with a resolution varying from 6 Å to 12 Å (i.e., only a few 3D coordinate positions are known for the input structure). This set has maximum sequence similarity (MSI) below 30% to the training set. Running the model will output a potential sequence corresponding to the input low-resolution protein structure. A comparison was made of the Fold2Seq model's performance on this set with that of another structure-based method (e.g., Graph trans) and principle-driven (physics based) methods (e.g., RosettaDesign). Since fold information is not available for these low-resolution structures, a structure-level sequence recovery ($sr_{structure}$) demonstrates that Fold2Seq outperforms other baselines. AsFold2Seq model 300 uses the high-level fold information (by re-scaling the structure, discretizing the space, and smoothing the spatial secondary structure element information by neighborhood averaging), the method's performance is less sensitive compared to RosettaDesign or Graph trans, when test structures are of lower resolution.

With respect to use of the Fold2Seq model architecture of FIG. 3B to perform a design task where the input structures have a region(s) of missing residues (i.e., structures that have a percentage, e.g., 5%, 10%, etc., that are incomplete). in order to mimic the real-world scenario, for every protein in an (out-of-distribution or OD) test set, the method first selects a stretch of residues at random starting positions with length p, for which residue information was removed. Running the model will output a potential sequence corresponding to the input incomplete protein structure. Comparing the Fold2Seq method with Graph trans at p={5%, 10%, 15%, 20%, 25%, 30%} it is demonstrated that as p increases, the Fold2Seq method outperforms Graph trans with a consistent margin.

With respect to use of the Fold2Seq model architecture of FIG. 3B applied to a structural ensemble of NMR structures (i.e., multiple structures, where each input structure is different $y_i, y_2, \ldots y_n$), a method first filters the NMR structures from two test sets and obtains proteins (e.g., 57 proteins) in 30 folds from the (in-distribution or ID) set and 30 proteins in 10 folds from the OD set. On average each protein has around 20 structures. Handling NMR ensembles using Fold2Seq is straightforward, in that, after obtaining the voxel-based features through eq. 1) for each model (structure) within one NMR ensemble, they are simply averaged across all models. Running the model will output a potential sequence that potentially folds according to each of the multiple input protein structures $y_1, y_2, \ldots y_n$. Results show that Fold2Seq performs better on both ID and OD proteins, when ensemble structure information is available. This is consistent with the hypothesis that fold representation better captures the structural variations present within a single fold.

FIG. 2 depicts a computer system 100 for building, training and using the Fold2Seq transformer models of FIGS. 3A, 3B that learns a 3D protein structure fold representation (e.g., learn a 1D protein sequence) from the 3D voxels of density of secondary structure elements according to embodiments herein. In some aspects, system 100 may include a computing device, a mobile device, or a server. In some aspects, computing device 100 may include, for example, personal computers, laptops, tablets, smart devices, smart phones, or any other similar computing device. It is to be understood that the computer system depicted in FIG. 2 is only one example of a suitable processing system and is not intended to suggest any limitation as to the scope of use or functionality of embodiments of the present invention. For example, the system shown may be operational with numerous other general-purpose or special-purpose computing system environments or configurations. Examples of well-known computing systems, environments, and/or configurations that may be suitable for use with the system shown in FIG. 2 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computing system 100 includes one or more hardware processors 152A, 152B, a memory 150, e.g., for storing an operating system and application program instructions, a network interface 156, a display device 158, an input device 159, and any other features common to a computing device. In some aspects, computing system 100 may, for example, be any computing device that is configured to communicate with one or more web-sites 125 including a web- or cloud-based server 120 over a public or private communications network 99. For instance, a web-site 125 may include a server including a protein structures data source, e.g., database 130 that collects three-dimensional structural data of large biological molecules, such as proteins, and enables access to them for use in Fold2seq encoder model training.

In the embodiment depicted in FIG. 2, processors 152A, 152B may include, for example, a microcontroller, Field Programmable Gate Array (FPGA), or any other processor that is configured to perform various operations such as Control Processing Units (CPUs), Graphics Processor Units (GPUs). Additionally shown are the communication channels or busses 140, e.g., wired connections such as data bus lines, address bus lines, Input/Output (I/O) data lines, etc., for routing signals between the various components of system 100. For example, bus 140 operably couples various system components, including memory 150 to processors 152A, 152B, and can represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Processors 152A, 152B are configured to execute method instructions as described below. These instructions may be stored, for example, as programmed modules in a further associated memory storage device 150. The processors 152A, 152B may execute one or more modules that are loaded from memory 150, where the program module(s) embody software (program instructions) that cause the processor to perform one or more method embodiments. In some embodiments, program modules may be programmed into the integrated circuits of the processor 152A, 152B, loaded from memory 150, storage system 160, network 99 and/or combinations thereof As an example, a transformer model can be trained on 2 Tesla K80 GPUs, with batch size 128. In every training stage, up to 200 epochs can be trained with an early stopping strategy based on the loss on the validation set.

The computer system may include a variety of computer system readable media. Such media may be any available media that is accessible by computer system, and it may include both volatile and non-volatile media, removable and non-removable media.

For example, memory 150 may include, for example, non-transitory computer readable media in the form of volatile memory, such as random access memory (RAM) and/or cache memory or other forms. Memory 150 may include, for example, other removable/non-removable, volatile/non-volatile storage media. By way of non-limiting examples only, memory 150 may include a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Computer system 100 may further include other removable/non-removable, volatile/non-volatile computer system storage media. By way of example only, a storage system 160 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 140 by one or more data media interfaces.

Network interface 156 is configured to transmit and receive data or information to and from a web-site server 120, e.g., via wired or wireless connections. For example, network interface 156 may utilize wireless technologies and communication protocols such as Bluetooth®, WIFI (e.g., 802.11a/b/g/n), cellular networks (e.g., CDMA, GSM, M2M, and 3G/4G/4G LTE/5G), near-field communications systems, satellite communications, via a local area network (LAN), via a wide area network (WAN), or any other form of communication that allows computing device 100 to transmit information to or receive information from the server 120. For example, interface 156 may include any devices (e.g., network card, modem, etc.) that enable the computer system to communicate with one or more other computing devices. Network interface 156 can include a network adapter that communicates with the other components of computer system via bus 140.

Display 158 may include, for example, a computer monitor, television, smart television, a display screen integrated into a personal computing device such as, for example, laptops, smart phones, smart watches, virtual reality headsets, smart wearable devices, or any other mechanism for displaying information to a user. In some aspects, display 158 may include a liquid crystal display (LCD), an e-paper/e-ink display, an organic LED (OLED) display, or other similar display technologies. In some aspects, display 158 may be touch-sensitive and may also function as an input device.

Input device 159 may include, for example, a keyboard, a mouse, a touch-sensitive display, a keypad, a microphone, or other similar input devices or any other input devices that may be used alone or together to provide a user with the capability to interact with the computing device 100.

It should be understood that although not shown, other hardware and/or software components could be used in conjunction with the computer system. Examples include, but are not limited to: microcode, device drivers, redundant processing units, external disk drive arrays, RAID systems, tape drives, and data archival storage systems, etc.

With respect to configuring the computer system 100 as a tool for solving the inverse protein folding problem, to accelerate prediction of sequences that can represent a received folded protein structure, a storage system 160 may be configured for temporarily storing transformer model training datasets 161 including sequences x and corresponding vectors forming protein fold representations y. The provided local memory 160 is further useful for the creating/storing data structures, e.g., tensor representations, vectors, matrices, parameters such as the model dimension (e.g., $d_{model}$, number of heads, number of layers, epochs, training iterations, etc.), hyperparameters, 3D coordinates in a voxel grid space for graphic representation of protein structures, i.e., for representing protein folds and/or sequences for training and prediction processing, and loss values used by the transformer model architecture to train the sequence-to-sequence model regularized by the sequence intra-domain loss $L_1$, and used to train the fold-to-sequence model regularized by the fold intra-domain loss and the cross-domain loss $L_2$.

Memory storage device 160 may be an attached, or a remote memory storage device, e.g., a database, accessible via a remote network connection for input to the system 100.

As mentioned, memory 150 of computer system 100 further stores processing modules that include programmed instructions adapted to invoke operations for predicting more accurate alternative sequences that fold into target 3D structures based on their graphical representations.

In one embodiment, one of the programmed processing modules stored at the associated memory 150 include a module 165 that is provided with computer readable instructions, data structures, program components and application interfaces for selecting and receiving graphical data representing a 3D protein or like molecule structure, e.g., from a protein structures data source web-site source database 130, and/or for receiving 3D structures of proprietary target proteins derived from other sources.

A further programmed processing module includes a graphics handler module 170 provided with computer readable instructions, data structures, program components and application interfaces for processing the 3D protein structures to re-scale, discretize, and form features from the received protein structure for the 3D voxel representation of the density of SSEs of a received protein structure in a 3D coordinate system as shown in FIG. 1.

A further programmed processing module includes a neural network processing module 175 that is provided with computer readable instructions, data structures, program components and application interfaces (APIs) for implementing Pytorch machine learning framework including application program interfaces for accessing libraries, models, classes (e.g., encoder class, decoder class, transformer class, including embedding, positional encoding, multi-headed attention classes, etc.), objects, extensions, and other tools and machine language (ML) learning components for building/training one or more layers of the transformer encoder/decoder model of FIG. 4.

In one embodiment, the transformer model 175 can include one or more deep learning neural network (DNN) models such as a feed-forward layers, including one or more of: convolution neural network (CNN), a graph CNN, multi-layer perceptrons (MLP) or a recurrent neural network (RNN). The deep learning models can be written in Python using the TensorFlow library.

A further programmed processing module includes a transformer sequence encoder processing module 180 that is provided with computer readable instructions, data structures, program components and application interfaces (APIs) for implementing sequence-to-sequence model training of FIGS. 5, 6 using Pytorch modules and training model classes.

A further programmed processing module includes a transformer structure encoder processing module 185 that is provided with computer readable instructions, data structures, program components and application interfaces (APIs) for implementing fold-to-sequence model training of FIGS. 5, 6 using Pytorch modules and training model classes. This module further comprises the structure encoder/sequence decoder for decoding sequences during the training and inference stages, e.g., by calling each of the program modules for inferring alternative protein sequences/designs given target 3D protein structures.

A further programmed processing module includes a module 190 that is provided with computer readable instructions, data structures, program components and application interfaces (APIs) for training the transformer model framework of FIG. 3A to learn a joint embedding across two domains including the computing of the inter-domain and cross-domain losses in the manner described herein using Pytorch modules and classes.

As further shown, memory 150 includes a supervisory program 110 having instructions for configuring the computing system 100 to invoke the building/training one or more layers of a transformer encoder/decoder model training and inferring operations described herein, i.e., provide application program interfaces for calling each of the program modules for inferring protein sequences/designs given target 3D protein structures.

In some embodiments, the computer system may be described in the general context of computer system executable instructions, embodied as program modules stored in memory 150, being executed by the computer system. Generally, program modules may include routines, programs, objects, components, logic, data structures, and so on that perform particular tasks and/or implement particular input data and/or data types in accordance with the present invention (see e.g., FIGS. 3A, 3B).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The corresponding structures, materials, acts, and equivalents of all elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method to design biological sequences using inverse folding of three-dimensional structures, the method comprising:

using a first transformer model encoder as part of a sequence-to-sequence model running on a hardware processor to generate latent sequence representations of corresponding receive an input one-dimensional biological sequences of nucleotides or amino acids represented as text which correspond with respective three-dimensional biological structures, a generated latent sequence representation of the generated latent sequence representations comprising an encoded vector representation of a one-dimensional biological sequence of the one-dimensional biological sequences in a first latent space;

using a second transformer model encoder as part of a fold-to-sequence model running on the hardware processor to generate respective latent fold representations of the respective three-dimensional biological structures corresponding to the respective input one-dimensional biological sequences, a generated latent fold representation of the generated latent fold representations comprising an encoded vector representation of a three-dimensional biological structure of the three-dimensional biological structures in a second latent space, wherein the three-dimensional biological structure comprises a density of structural elements represented in 3D voxels of a 3D voxel grid space, each 3D voxel comprising a feature representation comprising a probabilistic approximation determined from contributions of residues within neighboring voxels;

training, using the hardware processor, a transformer model decoder to learn a joint latent space between said generated latent sequence representations of input one-dimensional biological sequences and said generated respective latent fold representations of the respective three-dimensional biological structures corresponding to the input one-dimensional biological sequences;

receiving, at said second transformer model encoder running at the hardware processor, an encoded representation of a target three-dimensional biological structure;

generating, using said second transformer model encoder, an encoded vector representation of said received target three-dimensional biological structure in the second latent space; and inputting the encoded vector representation of the target three-dimensional biological structure to said trained transformer model decoder running on said hardware processor, said trained transformer model outputting, in response, an alternative one-dimensional sequence of nucleotides or amino acids which will result in a similar three-dimensional biological structure having the same folds as said target three-dimensional biological structure.

2. The method of claim 1, wherein said three-dimensional biological structure is a protein, said training the transformer model decoder comprising:

running a supervised learning task for classifying a fold representation of the protein using an encoded vector representation of the input one-dimensional biological sequence of the protein in the first latent space and using an encoded vector representation of the input three-dimensional biological sequence corresponding to the input protein sequence in the second latent space.

3. The method of claim 2, wherein the sequence-to-sequence model comprises said first transformer encoder and said trained transformer decoder, said method further comprising:
comparing classified protein folds between two samples of input one-dimensional biological sequences of two proteins having similar fold representations and determining a resulting closeness of their encoded vector representations in the first latent space; and
training the sequence-to-sequence model by regularizing by a sequence intra-domain loss function comprising a sequence-to-sequence reconstruction loss and a first intra-domain similarity loss, determined by the resulting closeness of their encoded vector representations in the first latent space.

4. The method of claim 3, wherein the fold-to-sequence model comprises said second transformer encoder and said trained transformer decoder, said method further comprising:
comparing classified protein folds between two samples of input three-dimensional biological structures of proteins having similar fold representations and determining a resulting closeness of their encoded vector representations in the second latent space; and
subsequently training the fold-to-sequence model by regularizing by a fold-to-sequence reconstruction loss and a second intra-domain similarity loss determined by the resulting closeness of their encoded vector representations in the second latent space.

5. The method of claim 4, wherein said fold-to-sequence model is further regularized using a cosine similarity cross domain loss, said method further comprising:
determining a cosine similarity cross-domain loss by maximizing a cosine similarity between encoded vector representations in said first latent space and said second latent space, said determining the cosine similarity cross domain loss comprising:
computing a similarity matrix as a product between said encoded vector representations in said first latent space and said second latent space, wherein an i'th row in said similarity matrix represents a similarity between an i'th position in a fold and every position of a sequence;
performing upon said similarity matrix a row-wise average pooling with a defined kernel size; and
performing a row-wise max operation to result in averaging a score of continuous positions in the sequence as defined by the kernel size; and
obtaining a final similarity score by averaging over all positions in the fold.

6. The method of claim 5, wherein said fold-to-sequence model is further regularized using a cyclic cross domain loss, said method further comprising:
determining a cyclic loss cross-domain loss responsive to a difference between an encoded latent state of an argmax of an alternative one-dimensional sequence output of the fold-to-sequence model and a native encoded latent state of the input one-dimensional biological sequence of the corresponding three-dimensional biological structure using the first transformer model encoder.

7. The method of claim 2, further comprising:
obtaining a fold representation of a protein by:
re-scaling a three-dimensional (3D) protein structure to fit within the 3D voxel grid space having discretized voxels of predetermined size;
featurizing the protein structure to obtain protein structural element features for individual 3D voxels from the protein structure content.

8. The method of claim 7, wherein the featurizing the protein structure further comprises:
denoting a position of each residue by its alpha carbon as a 3D coordinate within the 3D voxel grid space; and
assigning a secondary structure label to each residue, said secondary structure labels comprising one selected from: a helix, a beta strand, a loop and a bend/turn.

9. The method of claim 8, further comprising:
generating an encoded representation of an input three-dimensional biological structure by applying a sinusoidal 3D positional encoding to the featurized protein structure in the 3D voxel grid space.

10. The method of claim 1, wherein the structural elements represented in 3D voxels comprise secondary structure elements selected from the group comprising: a helix, beta-sheet, beta-strand, loop, bend, and turn, wherein a 3D voxel of the 3D voxels includes a representation of said secondary structure element as an associated label assigned to a residue.

11. A computer program product for designing biological sequences using inverse folding of three-dimensional structures, the computer program product comprising a non-transitory storage medium readable by a processing circuit and storing computer readable instructions run by the processing circuit for performing a method comprising:
using a first transformer model encoder as part of a sequence-to-sequence model to generate latent sequence representations of corresponding input one-dimensional biological sequences of nucleotides or amino acids represented as text which correspond with respective three-dimensional biological structures, a generated latent sequence representation of the generated latent sequence representations comprising an encoded vector representation of a one-dimensional biological sequence of the one-dimensional biological sequences in a first latent space;
using a second transformer model encoder as part of a fold-to-sequence model to generate respective latent fold representations of the respective three-dimensional biological structures corresponding to the respective input one-dimensional biological sequences, a generated latent fold representation of the generated latent fold representations comprising an encoded vector representation of a three-dimensional biological structure of the three-dimensional biological structures in a second latent space, wherein the three-dimensional biological structure comprises a density of structural elements represented in 3D voxels of a 3D voxel grid space, each 3D voxel comprising a feature representation comprising a probabilistic approximation determined from contributions of residues within neighboring voxels;
training a transformer model decoder to learn a joint latent space between said generated latent sequence representations of input one-dimensional biological sequences and said generated respective latent fold representations of the respective three-dimensional biological structures corresponding to the input one-dimensional biological sequences;

receiving, at said second transformer model encoder running at the processing circuit, an encoded representation of a target three-dimensional biological structure;

generating, using said second transformer model encoder, an encoded vector representation of said received target three-dimensional biological structure in the second latent space; and inputting the encoded vector representation of the target three-dimensional biological structure to said trained transformer model decoder running on said processing circuit, said trained transformer model outputting, in response, an alternative one-dimensional sequence of nucleotides or amino acids which will result in a similar three-dimensional biological structure having the same folds as said target three-dimensional biological structure.

12. The computer program product as claimed in claim 11, wherein said three-dimensional biological structure is a protein, said training the transformer model decoder comprising:

running a supervised learning task for classifying a fold representation of the protein using an encoded vector representation of the input one-dimensional biological sequence of the protein in the first latent space and using an encoded vector representation of the input three-dimensional biological sequence corresponding to the input protein sequence in the second latent space.

13. The computer program product as claimed in claim 12, wherein the sequence-to-sequence model comprises said first transformer encoder and said trained transformer decoder, said method further comprising:

comparing classified protein folds between two samples of input one-dimensional biological sequences of two proteins having similar fold representations and determining a resulting closeness of their encoded vector representations in the first latent space; and training the sequence-to-sequence model by regularizing by a sequence intra-domain loss function comprising a sequence-to-sequence reconstruction loss and a first intra-domain similarity loss determined by the resulting closeness of their encoded vector representations in the first latent space.

14. The computer program product of claim 13, wherein the fold-to-sequence model comprises said second transformer encoder and said trained transformer decoder, said method further comprising:

comparing classified protein folds between two samples of input three-dimensional biological structures of proteins having similar fold representations and determining a resulting closeness of their encoded vector representations in the second latent space; and subsequently training the fold-to-sequence model by regularizing by a fold-to-sequence reconstruction loss and a second intra-domain similarity loss determined by the resulting closeness of their encoded vector representations in the second latent space.

15. The computer program product of claim 14, wherein said fold-to-sequence model is further regularized using a cosine similarity cross domain loss, said method further comprising:

determining a cosine similarity cross-domain loss by maximizing a cosine similarity between encoded vector representations in said first latent space and said second latent space, said determining the cosine similarity cross domain loss comprising:

computing a similarity matrix as a product between said encoded vector representations in said first latent space and said second latent space, wherein an i'th row in said similarity matrix represents a similarity between an i'th position in a fold and every position of a sequence;

performing upon said similarity matrix a row-wise average pooling with a defined kernel size; and performing a row-wise max operation to result in averaging a score of continuous positions in the sequence as defined by the kernel size; and obtaining a final similarity score by averaging over all positions in the fold.

16. The computer program product of claim 15, wherein said fold-to-sequence model is further regularized using a cyclic cross domain loss, said method further comprising:

determining a cyclic loss cross-domain loss responsive to a difference between an encoded latent state of an argmax of an alternative one-dimensional sequence output of the fold-to-sequence model and a native encoded latent state of the input one-dimensional biological sequence of the corresponding three-dimensional biological structure using the first transformer model encoder.

17. The computer program product of claim 12, wherein said method further comprises:

obtaining a fold representation of a protein by:

re-scaling a three-dimensional (3D) protein structure to fit within a 3D voxel grid space having discretized voxels of predetermined size;

featurizing the protein structure to obtain protein structural element features for individual voxels from the protein structure content.

18. The computer program product of claim 17, wherein said method further comprises:

generating an encoded representation of an input three-dimensional biological structure by applying a sinusoidal 3D positional encoding to the featurized protein structure in the 3D voxel grid space.

19. The computer program product as claimed in claim 11, wherein the structural elements represented in 3D voxels comprise secondary structure elements selected from the group comprising: a helix, beta-sheet, beta-strand, loop, bend, and turn, wherein a 3D voxel of the 3D voxels includes a representation of said secondary structure element as an associated label assigned to a residue.

20. A computer-implemented system to design biological sequences using inverse folding of three-dimensional structures, the system comprising:

a memory storage device; and a hardware processor coupled to said memory storage device and configured to perform a method to:

use a first transformer model encoder as part of a sequence-to-sequence model to generate latent sequence representations of corresponding input one-dimensional biological sequences of nucleotides or amino acids represented as text which correspond with respective three-dimensional biological structures, a generated latent sequence representation of the generated latent sequence representations comprising an encoded vector representation of a one-dimensional biological sequence of the one-dimensional biological sequences in a first latent space;

use a second transformer model encoder as part of a fold-to-sequence model to generate respective latent fold representations of the respective three-dimensional biological structures corresponding to the respective input one-dimensional biological sequences, a generated latent fold representation of the generated latent sequence representations comprising an encoded vector representation of a three-dimensional biological structure of the three-dimensional biological structures in a second latent space, wherein the three-dimensional biological structure comprises a density of structural elements represented in 3D voxels of a 3D voxel grid space, each 3D voxel comprising a feature representation comprising a probabilistic approximation determined from contributions of residues within neighboring voxels;

train a transformer model decoder to learn a joint latent space between said generated latent sequence representations of input one-dimensional biological sequences and said generated respective latent fold representations of the respective three-dimensional biological structures corresponding to the input one-dimensional biological sequences;

receive, at said second transformer model encoder, an encoded representation of a target three-dimensional biological structure;

generate, using said second transformer model encoder, an encoded vector representation of said received target three-dimensional biological structure in the second latent space; and input the encoded vector representation of the target three-dimensional biological structure to said trained transformer model decoder, said trained transformer model outputting, in response, an alternative one-dimensional sequence of nucleotides or amino acids which will result in a similar three-dimensional biological structure having the same folds as said target three-dimensional biological structure.

21. The computer-implemented system of claim 20, wherein said three-dimensional biological structure is a protein, wherein to train the transformer model decoder, the hardware processor is further configured to:

run a supervised learning task for classifying a fold representation of the protein using an encoded vector representation of the input one-dimensional biological sequence of the protein in the first latent space and using an encoded vector representation of the input three-dimensional biological sequence corresponding to the input protein sequence in the second latent space.

22. The computer-implemented system of claim 21, wherein the sequence-to-sequence model comprises said first transformer encoder and said trained transformer decoder, said hardware processor is further configured to:

compare classified protein folds between two samples of input one-dimensional biological sequences of two proteins having similar fold representations and determining a resulting closeness of their encoded vector representations in the first latent space; and train the sequence-to-sequence model by regularizing by a sequence intra-domain loss function comprising a sequence-to-sequence reconstruction loss and a first intra-domain similarity loss determined by the resulting closeness of their encoded vector representations in the first latent space.

23. The computer-implemented system of claim 22, wherein the fold-to-sequence model comprises said second transformer encoder and said trained transformer decoder, said hardware processor is further configured to:

compare classified protein folds between two samples of input three-dimensional biological structures of proteins having similar fold representations and determining a resulting closeness of their encoded vector representations in the second latent space; and subsequently train the fold-to-sequence model by regularizing by a fold-to-sequence reconstruction loss and a second intra-domain similarity loss determined by the resulting closeness of their encoded vector representations in the second latent space.

24. The computer-implemented system of claim 23, wherein said fold-to-sequence model is further regularized using a cosine similarity cross domain loss and a cyclic cross domain loss, said hardware processor is further configured to:

determine a cosine similarity cross-domain loss by maximizing a cosine similarity between encoded vector representations in said first latent space and said second latent space, said determining the cosine similarity cross domain loss comprising:

computing a similarity matrix as a product between said encoded vector representations in said first latent space and said second latent space, wherein an i'th row in said similarity matrix represents a similarity between an i'th position in a fold and every position of a sequence;

performing upon said similarity matrix a row-wise average pooling with a defined kernel size; and performing a row-wise max operation to result in averaging a score of continuous positions in the sequence as defined by the kernel size; and obtain a final similarity score by averaging over all positions in the fold, and determine the cyclic loss cross-domain loss responsive to a difference between an encoded latent state of an argmax of an alternative one-dimensional sequence output of the fold-to-sequence model and a native encoded latent state of the input one-dimensional biological sequence of the corresponding three-dimensional biological structure using the first transformer model encoder.

25. The computer-implemented system of claim 20, wherein the structural elements represented in 3D voxels comprise secondary structure elements selected from the group comprising: a helix, beta-sheet, beta-strand, loop, bend, and turn, wherein a 3D voxel of the 3D voxels includes a representation of said secondary structure element as an associated label assigned to a residue.

* * * * *